Figure 1:
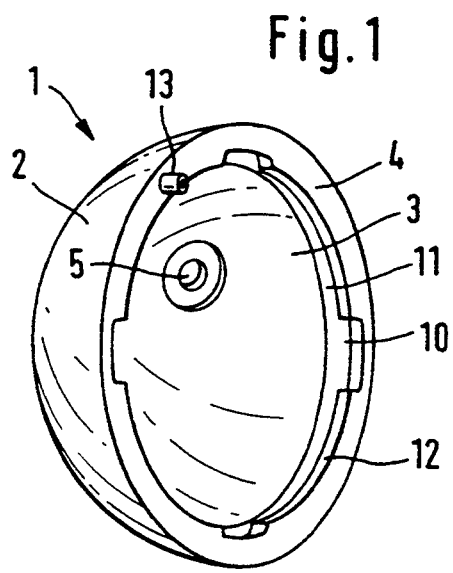

United States Patent
Keller

Patent Number: 5,360,451
Date of Patent: Nov. 1, 1994

[54] ACETABULAR CUP FOR A HIP JOINT ENDOPROSTHESIS

[75] Inventor: Arnold Keller, Kayhude, Germany

[73] Assignee: Waldemar Link GmbH & Co., Hamburg, Germany

[21] Appl. No.: 118,941

[22] Filed: Sep. 9, 1993

[30] Foreign Application Priority Data

Sep. 15, 1992 [DE] Germany ............ 9212419[U]

[51] Int. Cl.$^5$ ............................................. A61F 2/32
[52] U.S. Cl. ............................................. 623/22
[58] Field of Search .................. 623/16, 18, 19, 22, 623/23

[56] References Cited

U.S. PATENT DOCUMENTS

| | | | |
|---|---|---|---|
| 4,159,544 | 7/1979 | Termanini | 623/22 |
| 4,623,351 | 11/1986 | Church | 623/22 |
| 4,904,265 | 2/1990 | MacCollum et al. | 623/22 |
| 5,002,577 | 3/1991 | Bolesky et al. | 623/22 |
| 5,133,763 | 7/1992 | Mullers | 623/22 |
| 5,226,917 | 7/1993 | Schryver | 623/22 |

FOREIGN PATENT DOCUMENTS

| | | | |
|---|---|---|---|
| 0239485 | 3/1987 | European Pat. Off. | 623/22 |
| 0340175 | 3/1989 | European Pat. Off. | 623/22 |
| 0470912 | 6/1991 | European Pat. Off. | 623/22 |
| 2649005 | 7/1989 | France | 623/22 |
| WO84/03432 | 9/1984 | WIPO | 623/22 |

*Primary Examiner*—David Isabella
*Attorney, Agent, or Firm*—Chilton, Alix & Van Kirk

[57] ABSTRACT

Acetabular cup for a hip joint endoprosthesis consisting of a socket to be introduced into the hip bone, and an insert forming the joint surface. To secure the insert in the socket, a bayonet catch is provided with screw retention in the interacting edges of socket and insert. In the one edge an elongate depression is formed in the circumferential direction, into which depression there engages a screw head which projects from the other edge and which, with one end of the depression, forms a stop for finding the locking position. At this end of the elongate depression the latter comprises a bore into which the screw head can be screwed from the stop position, in order to secure the locking position.

12 Claims, 1 Drawing Sheet

U.S. Patent

Nov. 1, 1994

5,360,451

ACETABULAR CUP FOR A HIP JOINT ENDOPROSTHESIS

The invention relates to an acetabular cup for a hip joint endoprosthesis, consisting of a socket to be introduced into the hip bone, and an insert which forms the joint surface and which can be locked in the socket by means of a bayonet catch.

In a known acetabular cup of this type (EP-B 0.137 040) the bayonet catch can be fixed by means of a screw which engages in those edges of the socket and of the insert facing one another. A disadvantage of this solution is that the screw must be introduced as a small and separate part following the implantation of the prosthesis components, which can lead to difficulties under operating conditions, and that the particular position of rotation of the insert relative to the socket, in which position the screw holes are flush with one another, is difficult to find. In addition, the screw is not secured in the mounted and implanted state.

The invention avoids these disadvantages.

The elongate depression in the one of the two edges forms, together with the screw in the other of the two edges, a stop which defines the locking position of the bayonet catch. Since this stop (more precisely, the center line of the screw in the stop position) is flush with the bore matching the screw, which bore receives the screw for the purpose of fixing the locking position, the position in which the screw can be transferred to the securing position need not be sought first, but instead is obtained at once in the stop position. Since the screw is already pre-assembled as a stop element, it too does not need to be introduced first, but instead need only be transferred by means of appropriate rotation from the non-securing position to the securing position within the bore allocated to it. The introduction of the prosthesis is in this way made considerably easier. Also, by means of the arrangement according to the invention, the screw is secured positively. It is indeed prevented, by the bottom of the elongate depression, from moving completely out from the intended position.

The elongate depression is expediently provided in the edge of the insert, while the screw is pre-assembled in the edge of the socket. However, the reverse is also conceivable.

If the longitudinal depression is provided in the edge of the insert, the bore provided for receiving the screw (in this case the screw head) has a continuation of smaller diameter which passes through to the outside and through which a screwdriver tool can be conveyed for transferring the screw from the stop position into the securing position.

Figure 2:
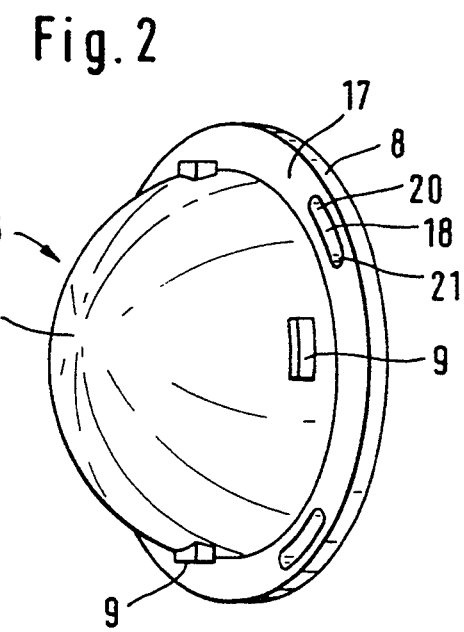
Figure 3:
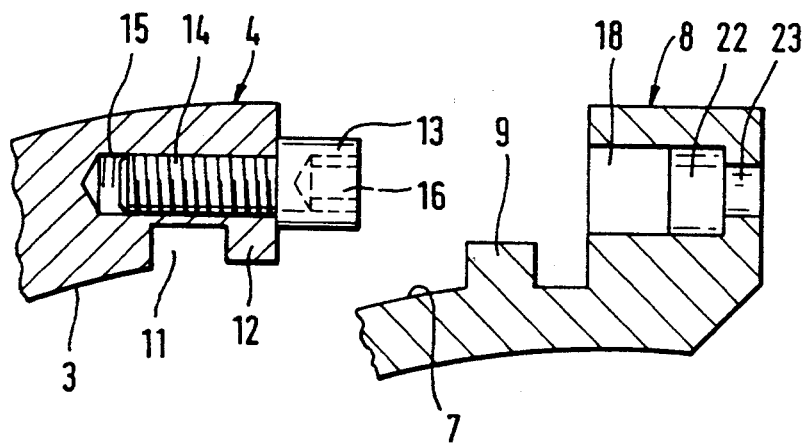
Figure 4:
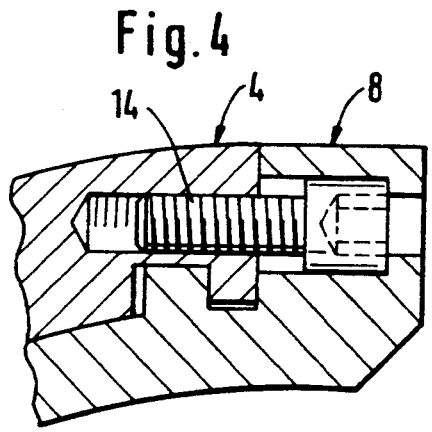
Figure 5:
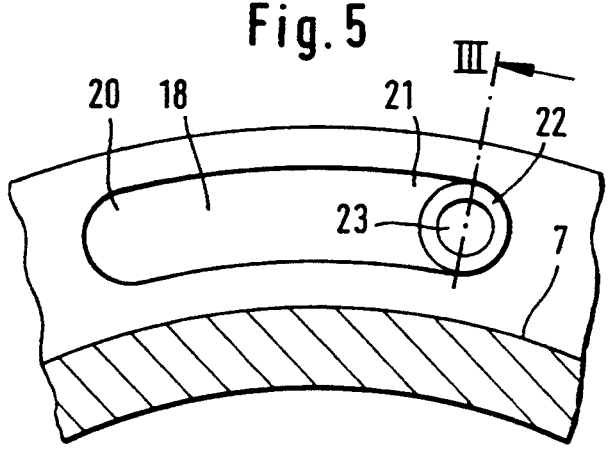

The invention is discussed in greater detail hereinbelow with reference to the drawing, which illustrates an advantageous exemplary embodiment and in which:

FIGS. 1 and 2 show perspective views of the sides of the socket and of the insert facing one another, FIGS. 3 and 4 show partial sections, on an enlarged scale, of the edges of the socket and of the insert in the separated and in the joined state, and FIG. 5 shows a partial view of the underside of the edge of the insert.

The socket 1, which can consist of metal, has an outer surface 2 designed in a known manner for anchoring in the bone, a spherical inner surface 3 and an edge 4. Bores 5 can be provided at a suitable point for additional screw-type anchoring in the bone.

The insert 6 has a spherical outer surface 7 matching the inner surface 3 of the socket 1, and an edge 8 which protrudes in the manner of a flange, and also a spherical inner surface for receiving the ball of a joint.

The edges 4 and 8 of the socket and of the insert, respectively, are provided with interacting mounting facilities, which are formed by bayonet projections 9 distributed over the circumference of the insert, radial depressions 10 for the passage of the bayonet projections 9 on the inner circumference of the edge 4 of the socket 1, and a circumferential groove 11 which, when the bayonet catch is in the locking state, receives the bayonet projections 9 and is delimited on the opening side by a collar 12, behind which the projections 9 engage snugly and which, in the area of the depressions 10, is recessesed for the passage of the projections 9.

On the end face of the socket edge there projects the head 13 of a screw 14 which is held in a threaded bore 15 in the socket edge 4 and has a key grip surface, preferably in the form of a hexagonal recessed hole 16.

The edge 8 of the insert has, at a number of points distributed over the circumference, and in the same number as the bayonet projections 9 and the recesseses 10 in the end face 17, which is opposite the end face of the socket edge 4, elongate depressions 18 which extend in the circumferential direction and whose width and depth are adapted to the corresponding dimensions of the screw head 13 so that the latter can be accommodated therein. The one end 20 of each elongate depression engages in each case over that point at which the screw head 13 can be situated in the socket edge 4 upon introduction of the insert into the socket, when the bayonet projections 9 are situated at the same point as the bayonet recesses 10. The other end 21 of the elongate depressions 18 is situated at that point where the screw head 13 is situated in the desired locking state, when the projections 9 engage behind the collar 12. The end 21 of the elongate depressions thus forms, together with the screw head 13, a stop which defines the locking position of the insert in the socket.

Provided at the end 21 of the elongate depression 18 is a bore 22 whose wall is flush with the end of the elongate depression and which is dimensioned for snugly receiving the screw head 13. When the insert is screwed into the locking position in the socket, in which position the screw head 13 bears on the end of the elongate depression 18, the screw head can be accordingly unscrewed a little in order to penetrate into the bore 22 and there effect the rotational fixing of the insert relative to the socket. For this purpose a bore 23 is provided through which a screwdriver tool, for example a hexagon socket screw key, can be introduced. The bore 23 has a smaller diameter than the screw head 13. Its narrowness compared to the bore 22 thus effects a securing of the screw 14 in position.

In order to introduce and secure the insert in the socket, it is therefore necessary simply to bring the bayonet catch into the locking position, till the screw head 13 bears on the end of the elongate depressions, in order then to unscrew the screw a little so that it enters sufficiently into the bore 22.

I claim:

1. An acetabular cup for a hip endoprosthesis comprising a socket to be introduced into the hip bone and an insert lockably assemblable on the socket, said insert forming a joint surface of the endoprosthesis, said socket and insert having cooperative bayonet catch means for assembling the insert on the socket and lockable retention means for locking the socket and the insert in their assembled relationship, said retention means comprising an elongated keyway on one of said socket and insert an da projectably adjustable key on the other of said socket and insert, said adjustable key cooperatively engaging said keyway during assembly, one end of said keyway having a key stop for assisting in positioning the key and a key receptor adjacent the stop for receiving said key upon positional adjustment of the key for lockably securing the socket and insert in said assembled relationship.

2. The acetabular cup of claim 1 wherein access means to said key receptor is provided to permit adjustable projection of said key into and out of said key receptor stop.

3. The acetabular cup of claim 1 wherein said key receptor is a bore aligned with said stop and said key includes a head portion sized to abut against said stop and fit within said bore.

4. The acetabular cup of claim 1 wherein one of said socket and insert includes a peripheral flange carrying said elongated keyway.

5. The acetabular cup of claim 1 wherein said elongated keyway extends circumferentially of the socket and insert assembly and includes a stop at said one end.

6. The acetabular cup of claim 1 wherein said key receptor includes a recess for snugly receiving said key.

7. The acetabular cup of claim 1 wherein said key includes a threaded portion for adjusting the projection thereof.

8. The acetabular cup of claim 1 wherein said keyway is carried by said insert and is in confronting relationship to said socket.

9. The acetabular cup of claim 8 wherein access means to said key receptor is provided to permit adjustable movement of said key into and out of said receptor.

10. The acetabular cup of claim 8 wherein said receptor is a bore aligned with said stop, said key including a head portion sized to abut said stop and fit within said bore.

11. The acetabular cup of claim 9 wherein said access means is of sufficient size to permit passage of a key adjusting tool therethrough for adjusting the projection of said key into and out of said receptor.

12. The acetabular cup of claim 11 wherein said access means includes an access passageway.

* * * * *